United States Patent
Vancza

(10) Patent No.: US 9,730,868 B2
(45) Date of Patent: Aug. 15, 2017

(54) COMPOSITION HAVING EARTH MATERIALS COMPRISING THE PIGMENT

(71) Applicant: MINA ATRAMENTUM, LLC, High Falls, NY (US)

(72) Inventor: Veleta Vancza, High Falls, NY (US)

(73) Assignee: MINA ATRAMENTUM, LLC, High Falls, NY (US)

( * ) Notice: Subject to any disclaimer, the term of this patent is extended or adjusted under 35 U.S.C. 154(b) by 0 days.

(21) Appl. No.: 14/640,572

(22) Filed: Mar. 6, 2015

(65) Prior Publication Data

US 2015/0328090 A1    Nov. 19, 2015

Related U.S. Application Data

(60) Provisional application No. 61/949,575, filed on Mar. 7, 2014.

(51) Int. Cl.
| | | |
|---|---|---|
| *A61K 9/14* | (2006.01) | |
| *A61K 8/19* | (2006.01) | |
| *A61Q 3/02* | (2006.01) | |
| *A61K 8/02* | (2006.01) | |

(52) U.S. Cl.
CPC .............. *A61K 8/19* (2013.01); *A61K 8/0241* (2013.01); *A61Q 3/02* (2013.01); *A61K 2800/20* (2013.01); *A61K 2800/412* (2013.01)

(58) Field of Classification Search
CPC ... A61K 6/23; A61K 6/17; A61K 6/38; A61K 8/19; A61K 6/835; A61K 2800/412; A61K 2800/436; A61K 2800/522; A61K 8/0258; A61Q 19/00; A61Q 1/12; A61Q 5/02; A61Q 17/04; A61Q 1/00; A61Q 1/08; A61Q 8/00
See application file for complete search history.

(56) References Cited

U.S. PATENT DOCUMENTS

| | | | |
|---|---|---|---|
| 3,713,870 A * | 1/1973 | Kaye | B05D 5/06 427/383.1 |
| 4,482,538 A | 11/1984 | Davies | |
| 4,857,306 A | 8/1989 | Roller | |
| 6,325,847 B1 | 12/2001 | Christie et al. | |
| 6,475,609 B1 * | 11/2002 | Whitney | B32B 7/02 428/212 |
| 6,631,723 B1 * | 10/2003 | Mullin | A45D 31/00 132/73 |
| 7,030,985 B2 | 4/2006 | Jager-Lezer et al. | |
| 7,582,285 B2 | 9/2009 | Krüger et al. | |
| 7,776,316 B2 | 8/2010 | Kolodziej et al. | |
| 2003/0019501 A1 | 1/2003 | Hirota et al. | |
| 2003/0077238 A1 | 4/2003 | Roovers et al. | |
| 2003/0185774 A1 | 10/2003 | Dobbs et al. | |
| 2007/0189996 A1 | 8/2007 | Weber et al. | |
| 2007/0199478 A1 | 8/2007 | Schlegl et al. | |
| 2007/0202135 A1 | 8/2007 | Ouellette | |
| 2008/0206173 A1 | 8/2008 | Weber et al. | |
| 2009/0013906 A1 | 1/2009 | Fischer et al. | |
| 2009/0022765 A1 | 1/2009 | Chung et al. | |
| 2010/0239620 A1 | 9/2010 | Butler et al. | |
| 2015/0328090 A1 | 11/2015 | Vancza | |

FOREIGN PATENT DOCUMENTS

| | | |
|---|---|---|
| EP | 1413284 A1 | 4/2004 |
| EP | 2147954 A1 | 1/2010 |
| EP | 2348076 A1 | 7/2011 |
| EP | 3064195 A1 | 9/2016 |
| FR | 2959665 A1 | 11/2011 |
| WO | 9936478 A1 | 7/1999 |

OTHER PUBLICATIONS

Anonymous: "GNPD—18K White Gold and Silver Top Coat", ID 2261496, Dec. 1, 2013 (Dec. 1, 2013), XP055279455, Retrieved from the Internet: URL:http://www.gnpd.com/sinatra/recordpage/2261496/from_search/M n YI H H9 DAQ/?page= 1 [retrieved on Jun. 9, 2016].
Extended European Search Report for EP Appln. No. 16155266.6, mailed on Jun. 20, 2016.

* cited by examiner

*Primary Examiner* — Nannette Holloman
(74) *Attorney, Agent, or Firm* — Schmeiser, Olsen & Watts, LLP

(57) ABSTRACT

A nail polish composition including a suspension base and a pigment, wherein at least 80% of the pigment is comprised of a noble metal, is provided. Furthermore, an associated method is also provided.

17 Claims, No Drawings

COMPOSITION HAVING EARTH MATERIALS COMPRISING THE PIGMENT

CROSS-REFERENCE TO RELATED APPLICATIONS

This application claims priority to and the benefit of U.S. Provisional Application No. 61/949,575, filed Mar. 7, 2014, and entitled "Composition Having Earth Materials Comprising the Pigment."

FIELD OF TECHNOLOGY

The following relates to a composition that utilizes earth materials as the pigment.

BACKGROUND

Nail lacquers or nail polishes can be purchased in a wide variety of colors. Traditionally, the color of the nail polish is created by using various pigments. Those pigments are typically synthetic materials. Moreover, traditional nail lacquers include toxic ingredients, such as formaldehyde, dibutyl phthalate (DBP), toluene, formaldehyde resin, and camphor.

Thus, a need exists for an apparatus and method for a nail lacquer composition that utilizes earth materials as the pigment, while also being free of common toxic ingredients.

SUMMARY

A first aspect relates generally to a composition comprising: a suspension base; and a pigment, wherein at least 80% of the pigment is comprised of a noble metal.

A second aspect relates generally to a composition comprising a suspension base; and a pigment for coloring the composition, the pigment having a weight/volume percentage with respect to a total volume of the composition above 5%, wherein the pigment comprises at least one of a noble metal and a gemstone.

A third aspect relates generally to a method of making a nail polish comprising adding a pigment to a suspension medium to form the nail polish, wherein at least 80% of the pigment is comprised of a noble metal.

The foregoing and other features of construction and operation will be more readily understood and fully appreciated from the following detailed disclosure, taken in conjunction with accompanying drawings.

DETAILED DESCRIPTION

A detailed description of the hereinafter described embodiments of the disclosed apparatus and method are presented herein by way of exemplification and not limitation with reference to the Examples provided herein. Although certain embodiments are shown and described in detail, it should be understood that various changes and modifications may be made without departing from the scope of the appended claims. The scope of the present disclosure will in no way be limited to the number of constituting components, the materials thereof, the shapes thereof, the relative arrangement thereof, etc., and are disclosed simply as an example of embodiments of the present disclosure.

As a preface to the detailed description, it should be noted that, as used in this specification and the appended claims, the singular forms "a", "an" and "the" include plural referents, unless the context clearly dictates otherwise.

Embodiments of the composition having earth materials, such as natural precious materials, forming the pigment may be a nail polish or nail lacquer that can that can be topically applied to fingernails or toe nails. Embodiments of the composition may also be applied to skin or other surfaces, inorganic or organic.

Embodiments of the composition may include a suspension medium and a pigment, wherein at least 80% of the pigment is comprised of a noble metal.

Embodiments of the composition may include a suspension medium. Embodiments of the suspension medium may be a suspension base, a base solution, a base nail polish, a base nail lacquer, a nail polish suspension base, a nail lacquer suspension base, a gel base, a gel polish, a high gloss base, a holographic base, a lacquer, a base coat, a top coat, a matte base, or any solution or suspension medium that can be combined with a pigment to form a nail polish composition. Further embodiments of the suspension medium may be clear or translucent. Embodiments of the suspension medium may be comprised of nitrocellulose. The suspension medium may also include various additives and fillers that are known to those having skill in the art. In an exemplary embodiment, the suspension medium may be may be 5-Free, meaning it may be free of 5 toxic ingredients found in many nail polishes—formaldehyde, dibutyl phthalate (DBP), toluene, formaldehyde resin and camphor.

Embodiments of the composition may also include a pigment. The pigment may be a material or a combination of materials used for coloring the composition. The composition may include one or more pigments. Embodiments of the pigments used in the composition may be metals, precious and semiprecious gemstones, precious metals, noble metals, and the like. For example, embodiments of the pigment that are precious metals are gold, platinum, and silver. Other materials that may be pigments include tin, aluminum, graphite, diamond, sapphire, emerald, turquoise, tourmaline, spinel, sugilite, citrine, lapis lazuli, quartz, iolite, nephrite, ruby, amethyst, peach jasper, garnet, red jasper, red carnelian, opal, topaz, aquamarine, peridot, hematite, tiger eye, sodalite, amazonite, and the like. Moreover, a percentage of the pigment of the composition may be made of only precious metals. In one embodiment, the composition may comprise a pigment, wherein the pigment is comprised of 100% of precious metals. In another embodiment, a percentage of the pigment is comprised of at least 80% precious metals. In yet another embodiment, the percentage of pigment that is formed by precious metals is between 80% and 100%. In other embodiments, the percentage of pigment comprised from precious metal is below 80%.

Furthermore, embodiments of the pigment comprising one or more precious metals may have an effective particle size. The size of the particle of the precious metal may affect the consistency of the nail lacquer. The desired particle size of the precious metal used as the pigment may depend on the precious metal. For instance, an effective particle size of 10-24K gold used as a pigment ranges between 3-10μ, but may also have an effective particle size as large as 80μ. An effective particle size of platinum used as a pigment ranges between 3-10μ, but may also have an effective particle size as large as 80μ. An effective particle size of silver used as a pigment ranges between 3-10μ, but may also have an effective particle size as large as 80μ. Other metals that may be used in combination with the precious metals of gold, silver, and platinum, such as aluminum, tin, and graphite may each also have an affective particle size. For instance, an effective particle size of aluminum used a pigment or as a pigment combination with a precious metal(s) ranges between 60-70μ, but may also have an effective particle size as large as 75μ. An effective particle size of tin used a pigment or as a pigment combination with a precious metal(s) ranges between 25-45μ, but may also have an effective particle size as large as 75μ. An effective particle size of graphite used a pigment or as a pigment combination with a precious metal(s) ranges between 6-10μ, but may also have an effective particle size as large as 20μ. Gemstones that may be used as a pigment or a combination with one or more precious metals may have an affective particle size that ranges between 3-25μ, but may also have an effective particle size as large as 80μ.

Embodiments of the composition may be described by the following examples. The following formulas have been applied in the following examples:

$$\frac{\text{Weight of Pigment(g)}}{\text{Total Vol (mL)}} \times 100,$$

which calculates the wt/vol %; and $$\frac{\text{Mass of Precious Metal (g)}}{\text{Total Mass of Pigment (g)}} \times 100,$$

which calculates the % of pigment comprised of precious metal.

EXAMPLE 1

The following composition is an embodiment of a composition using a suspension medium and a pigment only of 24K gold, having a particle size between 3-10μ:

| Weight of Precious Metal Pigment | Total Volume | Weight of Other Pigment | Wt/Vol % | % Pigment Made From Precious Metal |
|---|---|---|---|---|
| 2.5 g | 10 mL | N/A | 25% | 100% |

EXAMPLE 2

The following composition is an embodiment of a composition using a suspension medium and a pigment only of 22K gold, having a particle size between 3-10μ:

| Weight of Precious Metal Pigment | Total Volume | Weight of Other Pigment | Wt/Vol % | % Pigment Made From Precious Metal |
|---|---|---|---|---|
| 2 g | 10 mL | N/A | 20% | 100% |

EXAMPLE 3

The following composition is an embodiment of a composition using a suspension medium and a pigment only of gold, having a particle size between 3-10μ:

| Weight of Precious Metal Pigment | Total Volume | Weight of Other Pigment | Wt/Vol % | % Pigment Made From Precious Metal |
|---|---|---|---|---|
| 0.6 g | 10 mL | N/A | 6% | 100% |

EXAMPLE 4

The following composition is an embodiment of a composition using a suspension medium and a pigment being made of a combination of gold having a particle size between 3-10μ and graphite, having a particle size between 6-10μ:

| Weight of Precious Metal Pigment | Total Volume | Weight of Other Pigment | Wt/Vol % | % Pigment Made From Precious Metal |
|---|---|---|---|---|
| 0.6 g | 10 mL | 0.8 g | 6%:8% | 42.8% |

EXAMPLE 5

The following composition is an embodiment of a composition using a suspension medium and a pigment being made of platinum having a particle size between 70-75μ:

| Weight of Precious Metal Pigment | Total Volume | Weight of Other Pigment | Wt/Vol % | % Pigment Made From Precious Metal |
|---|---|---|---|---|
| 2.5 g | 10 mL | N/A | 25% | 100% |

EXAMPLE 6

The following composition is an embodiment of a composition using a suspension medium and a pigment being made of silver having a particle size between 3-10μ:

| Weight of Precious Metal Pigment | Total Volume | Weight of Other Pigment | Wt/Vol % | % Pigment Made From Precious Metal |
|---|---|---|---|---|
| 3 g | 10 mL | N/A | 30% | 100% |

EXAMPLE 7

The following composition is an embodiment of a composition using a suspension medium and a pigment being made of silver having a particle size between 40-45μ:

| Weight of Precious Metal Pigment | Total Volume | Weight of Other Pigment | Wt/Vol % | % Pigment Made From Precious Metal |
|---|---|---|---|---|
| 0.32 g | 10 mL | N/A | 3.2% | 100% |

EXAMPLE 8

The following composition is an embodiment of a composition using a suspension medium and a pigment being made of a combination of gold 24K having a particle size between 3-10µ and a synthetic pigment:

| Weight of Precious Metal Pigment | Total Volume | Weight of Other Pigment | Wt/Vol % | % Pigment Made From Precious Metal |
|---|---|---|---|---|
| 2.5 g | 10 ml | 0.625 g | 25%:6.25% | 80% |

EXAMPLE 9

The following composition is an embodiment of a composition using a suspension medium and a pigment being made of gold 24K having a particle size between 3-10µ and a synthetic pigment:

| Weight of Precious Metal Pigment | Total Volume | Weight of Other Pigment | Wt/Vol % | % Pigment Made From Precious Metal |
|---|---|---|---|---|
| 3 g | 10 mL | 0.5 g | 30%:5% | 85.7% |

EXAMPLE 10

The following composition is an embodiment of a composition using a suspension medium and a pigment being made of a combination of silver having a particle size between 3-10µ and an synthetic pigment:

| Weight of Precious Metal Pigment | Total Volume | Weight of Other Pigment | Wt/Vol % | % Pigment Made From Precious Metal |
|---|---|---|---|---|
| 3.5 g | 10 mL | 0.2 g | 20% | 94.6% |

Further examples include compositions that include other metals as the pigment, along with a suspension medium, wherein at least 80% of the pigment is comprised of metals and/or gemstones. For example, a composition including tin as the pigment may include 6.4 g in 10 mL, or 64% (wt/vol %). An embodiment of a composition that includes aluminum as the pigment may include 0.75 g in 10 mL, or 7.5% (wt/vol %). An embodiment of a composition that includes graphite as the pigment may include 0.8 g in 10 mL, or 8% (wt/vol %). An embodiment of a composition that includes a gemstone as the pigment may include 1 g in 10 mL, or 10% (wt/vol %).

Even further embodiments of a composition utilizing a precious metal as a pigment may include paints, such as automotive paints. In this embodiment, the suspension medium may be a waterborne or solventborne binder, as used in automotive basecoats. A precious metal may be added to the basecoat to form a composition that may be pneumatically sprayed onto automobiles or other vehicles or any surface that may require a basecoat of paint. Further, in this embodiment, a precious metal, such as gold 24K may a weight/volume percentage between 25-45% (e.g. 2.5-4.5 g in 10 mL binder), wherein a precious metal comprises 80% to a 100% of the pigment that forms the color of the paint.

The examples provided herein document a percentage of pigment comprised of a precious metal, but it is understood that the some suspension mediums that may be used in various embodiments of the composition may affect or comprise at least a portion of the pigment. Thus, the percentage pigment may only account for materials in the composition that are configured to or intended to cause coloration. In addition, the suspension medium may be separate elements forming the claimed composition.

While this disclosure has been described in conjunction with the specific embodiments outlined above, it is evident that many alternatives, modifications and variations will be apparent to those skilled in the art. Accordingly, the preferred embodiments of the present disclosure as set forth above are intended to be illustrative, not limiting. Various changes may be made without departing from the spirit and scope of the invention, as required by the following claims. The claims provide the scope of the coverage of the invention and should not be limited to the specific examples provided herein.

What is claimed is:

1. A composition comprising:
    a suspension base; and
    a pigment comprising either: (i) 100% noble metal, or (ii) at least 80% noble metal and a remaining percentage selected from the group consisting of a metal, a gemstone, a synthetic gemstone, and combinations thereof.

2. The composition of claim 1, wherein the noble metal has a particle size of 3-80µ.

3. The composition of claim 1, wherein the noble metal is at least one of gold, silver, and platinum.

4. The composition of claim 1, wherein the suspension base is a clear or translucent nail polish solution.

5. The composition of claim 1, wherein the suspension base is a binder for making a basecoat of automotive paint.

6. The composition of claim 1, wherein the composition is applied to at least one of a fingernail and a toenail.

7. A composition comprising:
    a suspension base; and
    a pigment for coloring the composition, the pigment having a weight/volume percentage with respect to a total volume of the composition above 5%;
    wherein the pigment consists of: (i) at least one noble metal, and (ii) one of: a metal, and a gemstone.

8. The composition of claim 7, wherein the pigment has a particle size of 3-80µ.

9. The composition of claim 7, wherein the noble metal includes at least one of gold, silver, and platinum.

10. The composition of claim 7, wherein the suspension base is a clear or translucent nail polish solution.

11. The composition of claim 7, wherein the suspension base is a binder for making a basecoat of automotive paint.

12. The composition of claim 7, wherein the composition is applied to at least one of a fingernail and a toenail.

13. A method of making a nail polish comprising:
    adding a pigment to a suspension medium to form the nail polish, wherein the pigment comprises either: (i) 100% noble metal, or (ii) at least 80% noble metal and a remaining percentage selected from the group consisting of a metal, a gemstone, a synthetic gemstone, and combinations thereof.

14. The method of claim 13, wherein the noble metal has a particle size of 3-80µ.

15. The method of claim 13, wherein the noble metal is at least one of gold, silver, and platinum.

16. The method of claim 13, wherein the suspension base is a clear or translucent nail polish solution.

17. The method of claim 13, wherein the composition is applied to at least one of a fingernail and a toenail.

* * * * *